United States Patent [19]

Iga et al.

[11] Patent Number: 5,000,959
[45] Date of Patent: Mar. 19, 1991

[54] LIPOSOME COMPOSITION AND PRODUCTION THEREOF

[75] Inventors: Katsumi Iga, Suita; Naoru Hamaguchi, Ibaraki; Yasuaki Ogawa, Otokuni, all of Japan

[73] Assignee: Takeda Chemical Industries, Ltd., Osaka, Japan

[21] Appl. No.: 350,029

[22] Filed: May 10, 1989

[51] Int. Cl.$^5$ ............................................. A61K 37/22
[52] U.S. Cl. .................... 424/450; 264/4.1; 264/4.3; 264/4.6
[58] Field of Search ................. 424/450; 264/4.3, 4.6, 264/4.1

[56] References Cited

U.S. PATENT DOCUMENTS

| | | | |
|---|---|---|---|
| 4,565,696 | 1/1986 | Heath et al. | 514/785 |
| 4,663,161 | 5/1987 | Mannino et al. | 424/450 |
| 4,844,904 | 7/1989 | Hamaguchi et al. | 424/450 |

OTHER PUBLICATIONS

Jonah, I. M., et al Biochimica et Biophysica Acta, 541, pp. 321–333 (1978).

Primary Examiner—Merrell C. Cashion, Jr.
Assistant Examiner—P. L. Prater
Attorney, Agent, or Firm—Wenderoth, Lind & Ponack

[57] ABSTRACT

The liposome compositions entrapping a drug are prepared by constituting the liposomal membrane with a saturated phospholipid and a glycolipid having sialic acid group. Thus obtained compositions circulate stably in blood for a long time after intravenous administration.

8 Claims, 3 Drawing Sheets

LIPOSOME COMPOSITION AND PRODUCTION THEREOF

The present invention relates to a liposome composition and a method of its production.

Drug delivery systems (DDS) have already been routinized in which a drug-entrapping liposome composition is intravenously administered and delivered to a particular target site in the subject's body [G. Gregoriadis et al.; Receptor-mediated Targeting of Drugs, Plenum Press, New York, pp. 243-266 (1980)].

The primary requirement of such DDS is that the liposome composition, after being intravenously administered, should stably circulate along with blood in the subject's body for a longer period of time than provided by conventional systems. Liposome, in essence, is not very stable in blood due to interaction between its membrane component lipid and the blood components such as lipoprotein. Also, intravenously administered liposome is likely to be recognized as a foreign substance by the reticuloendothelial system (RES) and thus likely to disappear from blood due to its physical morphology and biochemical properties. This is why the disappearance rate of intravenously administered liposome is higher than expected. It has therefore long been an important problem how liposome in blood should be stabilized to avoid recognition by RES and thus to delay its disappearance from blood. For example, one paper reports a case where cholesterol was added to liposome membrane composition to increase blood liposome stability [G. Scherphof et al.; "Liposomes: From physical structure to therapeutic applications," Elsevier, North Holland, pp. 310-311 (1981)]. However, the effect thus obtained can be said to vary widely depending on the original membrane composition of the liposome [J. Senior et al.; Biochemica et Biophysica Acta, 839, 1-8 (1985)]. Another paper reports that liposome delivery to RES can be suppressed by coating the surface of the liposome membrane with sialic acid using a glycoprotein having sialic acid group [M. Haga et al.; Chemical and Pharmaceutical Bulletin, 34, 2979-2988 (1986)]. It is also reported that such sialic acid-containing glycolipid, when administered as liposome, is distributed to the liver, a part of RES [A. Surolia et al.; Biochemica et Biophysica Acta, 497, 760-765 (1977)]. On the other hand, a liposome entrapping $^{14}C$-labeled EDTA was prepared using ganglioside, glycolipid containing sialic acid, and a natural unsaturated phospholipid in the presence or absence of cholesterol; distribution of EDTA in the subject's body was investigated after intravenous administration of the liposome composition [Biochemica et Biophysica Acta, 541, 321-333 (1978)].

As stated above, various attempts have been made to improve liposome membrane compositions; however, there is no efficient and highly practicable means of retarding the liposome disappearance from blood after intravenous administration. For example, the above-mentioned report of a study using ganglyoside states that blood EDTA concentration decreased below 5% at 1 hour following the intravenous injection of the obtained liposome, i.e., liposome disappearance from blood was very rapid.

In light of these conditions, the present inventors conducted investigations with the aim of modifying liposome membrane composition by adding various additives to make intravenously administered liposomes circulate stably with blood in the subject's body for longer periods, and developed the present invention.

Accordingly, the present invention provides: (I) a liposome composition entrapping a drug in liposome of which membrane is constituted by a phospholipid of which the acyl groups thereof are saturated acyl groups and a glycolipid having a sialic acid group, and (II) a method of producing a liposome composition entrapping a drug, which comprises (1) preparing an emulsion or a suspension containing a phospholipid of which acyl groups are saturated acyl groups and a glycolipid having a sialic acid group, wherein an effective amount of a drug added, and (2) subjecting the resulting emulsion or suspension to preparation of liposome vesicles so that the liposomal membrane is constituted by said phospholipid and glycolipid.

The phospholipids with saturated acyl groups (hereinafter referred to a phospholipids) used to produce the liposome composition of the present invention are glycerophospholipids and sphingophospholipids, both having saturated acyl groups. Examples of such phospholipids include those whose two acyl groups are saturated alkyls having 8 or more carbon atoms, acyl groups at least one of which is a saturated alkyl group having 10 or more carbon atoms, preferably 12 to 18 carbon atoms. It is preferable to use a phospholipid whose saturated acyl groups are both saturated alkyl having 12 to 18 carbon atoms. Such phospholipids include hydrogenated lecithin as obtained by hydrogenation of animal/plant-derived lecithin (e.g. yolk lecithin, soybean lecithin), semi-synthetically or total-synthetically obtained phosphatidylcholine comprising a combination of lauroyl, myristoyl, palmitoyl, stearoyl, etc., phosphatidylethanolamine, phosphatidylserine, phosphatidylglycerol, phosphatidylinositol, and sphingomyelin. In more detail, phospholipids having a phase transition temperature of 20° to 80° C. can be preferably used. Examples of such phospholipids include the following phospholipids, whose phase transition temperature (found value) is shown in parentheses: dimyristoylphosphatidylcholine (DMPC, 23.9° C.), palmitoylmyristoylphosphatidylcholine (PMPC, 27.2° C.), myristoylpalmitoylphosphatidylcholine (MPPC, 35.3° C.), dipalmitoylphosphatidylcholine (DPPC, 41.4° C.), stearoylpalmitoylphosphitdylcholine (SPPC, 44.0° C.), palmitoylstearoylphosphitadylcholine (PSPC, 47.4° C.), distearoylphosphatidylcholine (DSPC, 54.9° C.), dimyristoylphosphatidylethanolamine (DMPE, 50° C.), dipalmitoylphosphatidylethanolamine (DPPE, 60° C.), distearoylphosphatidylethanolamine (DSPE, over 60° C.), dimyristoylphosphatidylserine (DMPS, 38° C.), dipalmitoylphosphatidylserine (DPPS, 51° C.), distearoylphosphatidylserine (DSPS, over 50° C.), dimyristoylphosphatidylglycerol (DMPG, 23° C.), dipalmitoylphosphatidylglycerol (DPPG, 41° C.), distearoylphosphatidylglycerol (DSPG, 55° C.), dipalmitoylsphingomyelin (DPSM, 41° C.) and distearoylsphingomyelin (DSSM, 57° C.).

The glycolipid with sialic acid group used for the present invention is a sphingoglycolipid having one or more sialic acid groups, whether derived naturally or semi-synthetically (hereinafter also referred to as glycolipid). Here, sialic acid includes a group of neuramic acid and its acyl derivatives, such as N-acylneuramic acids, their esters, hydroxy derivatives and other derivatives. Specifically, such glycolipids include ganglyosides. The ganglyosides that can be used have saturated or unsaturated fatty acid residue with 16 to 28 carbon atoms and 1 to 4 sialic acid groups. Ganglyosides involve a large number of molecular species identified based on the number and position of bound sialic acids, and are exemplified by the following structural formulae:

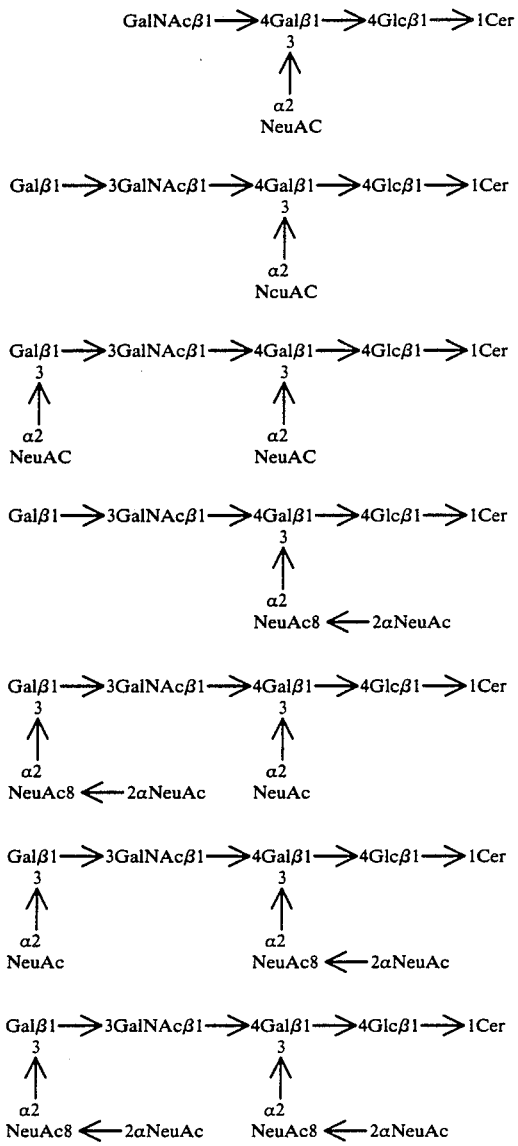

Cer: Ceramide  Glc: Glucose
Gal: Galactose  GalNAc: N-acetylgalactose
NeuAc: N-acetylneuraminic acid In the present invention, ganglyosides can be used singly or in combination. For example, a mixture of ganglyosides extracted and purified from living tissues (e.g. bovine brain) can be used [Biochemica et Biophysica Acta, 60, 359–365 (1962); Japanese Published Unexamined Patent Application No. 180719/1986]. Particularly, a mixture of ganglyosides having many sialic acid groups are molecule [phase transition temperature=30° C./46° C.; Biochemica et Biophysica Acta, 468, 11–20 (1977)] is preferably used.

In the present invention, the liposome membrane is composed of a phospholipid and a glycolipid, as described above.

The mixing ratio of phospholipid and glycolipid for the present invention is normally about 0.5 to 50 parts by weight, preferably about 2 to 20 parts by weight of glycolipid to 100 parts by weight of phospholipid.

The desired liposome membrane is prepared so that it would have a phase transition temperature of about 37° to 60° C., preferably about 40° to 55° C. Phase transition temperature can be adjusted by choosing an appropriate type of phospholipid mixing ratio, etc.

Since the phase transition temperature of a liposome membrane is generally near the theoretical value obtained by proportional allotment of the phase transition temperatures of respective constituent lipids to weight [cf. C. G. Knight; "Liposomes: From physical structure to therapeutic applications," Elsevier, North Holland, pp. 310–311 (1981)], it is possible to choose a lipid composition to obtain the desired membrane phase transition temperature on the basis of this relationship.

Usually, the membrane phase transition temperature can be adjusted so that it falls in the above-mentioned range using a mixing ratio as shown above; the purpose of the present invention can thus be accomplished, i.e., the disappearance of the obtained liposome composition from the blood is retarded. In preparing the desired liposome composition, stabilizers such as antioxidants and other additives (e.g. sugars serving as osmotic pressure regulators) may be used as long as they do not interfere with the purpose of the invention.

The present invention is characterized by the use of a phospholipid and glycolipid as described above to compose a liposome membrane; known techniques are used to compose the desired liposome membrane and to entrap a drug in the liposome. For example, the above liposome membrane composition containing a phospholipid with saturated acyl groups and a glycolipid with a sialic acid group is dissolved in an organic solvent such as diethyl ether, isopropyl ether or chloroform, and then emulsified with a drug solution to give a W/O type emulsion; the organic solvent is then evaporated under reduced pressure over 40° C. to yield reverse-phase evaporation vesicles (REV). It is also possible to obtain multilamellar vesicles (MLV) by mixing at a temperature exceeding 40° C. a drug solution and a film prepared by evaporating the organic solvent from the above lipid solution therein. MLV may be shaken using a probe type ultrasonic shaker to yield small unilamellar vesicles (SUV). Other methods of producing liposomes include the stable plurilamellar vesicle (SPLV) method (Japanese Published Unexamined Patent Application No. 500952/1984) and the dehydration-rehydration vesicle method [C. Kirby et al.; Biotechnology, Nov., 979 (1984)]. The glycolipid with a sialic acid group can also be used in dispersion in drug solution in place of in solution in organic solvent. It is also possible to use the method in which a drug-entrapping liposome composition is prepared using a phospholipid with a saturated acyl group and added to a dispersion containing a glycolipid with sialic acid group, followed by mixing while heating, to place the glycolipid with a sialic acid group on the already formed liposome membrane.

In cases where a fat-soluble drug with low water solubility is used, it may be dissolved in a lipid solution in organic solvent as mentioned above to give a liposome composition containing the drug. The present invention can work well in producing REV. The drug-entrapping liposome composition thus obtained can be adjusted to a preferable grain size as needed. For uniform of grain size, filter through Nuclepore filter or gel.

Also, it is preferable to use the present liposome composition after separating and removing the drug not entrapped in the liposome, for example by centrifugation, gel filtration or dialysis.

There is no particular limitation on the choice of a drug for the present invention, as long as the drug is used to compose a DDS. Examples of drugs which can be used include antitumor agents such as platinum compounds (e.g. cisplatin, carboplatin, spiroplatin), adriamycin, mitomycin C, actinomycin, ansamitocin, blemoycin, 5-FU and methotrexate; lymphokines such as natural or recombinant interferons ($\alpha,\beta,\gamma$) and natural or recombinant interleukin 2; bioactive peptides such as manganese superoxide dismutase (SOD) and its derivative superoxide dismutase PEG (PEG-5000) (Japanese Published Unexamined Patent Application No. 16685/1983; EPC Patent Publication No. 0210761); antifungal agents such as amphotericin, $\beta$-lactum antibiotics such as sulfazecin; aminoglycoside antibiotics such as gentamycin, streptomycin and kanamycin; vitamins such as cyanocobalamin and ubiquinone; antiprotozoan drugs such as meglemine antimonate; enzymes such as alkaline phosphatase; anticoagulation agents such as heparin; antiallergic agents such as amelexanox; immunopotentiating agents such as muramyldipeptide, muramyltripeptide and TMD-66 [Gann., 74 (2), 192–195 (1983)]; circulatory drugs such as propanalol; and metabolic potentiators such as glutathione.

The present invention is suitable for water-soluble drugs. Examples of such drugs include drugs having an octanol/water partition ratio below 10 in log value. An appropriate amount of drug entrapment is chosen with consideration of the type, effective dose etc. of the drug so that an effective amount is entrapped in the liposome.

The liposome composition of the present invention is generally used in the form of a solution or emulsion; it is dispersed in physiological saline, etc. in amounts chosen as appropriate to the purpose of the treatment, and intravenously administered by injection or drip infusion.

The liposome composition of the present invention circulates along with blood in the subject's body stably for long periods following intravenous administration; the toxicity intrinsic to the drug entrapped therein is thus modified, and the drug targeting effect for a particular lesion is enhanced. Therefore, the present liposome composition is useful for enhancing the sustained therapeutic effect of drugs. This stabilizing effect in blood is stronger than that of any liposome composition comprising a combination of a phospholipid with said unsaturated acyl groups and a glycolipid with said sialic acid group or combination of a phospholipid with saturated acyl groups and a glycolipid with no sialic acid group. Particularly, the liposome composition of the present invention entrapping an antitumor agent is expected to have an improved therapeutic effect when administered in hyperthermia treatment of cancer; in this case, a liposome composition having a membrane phase transition temperature of about 40° to 55° C. is preferable.

Figure 1:
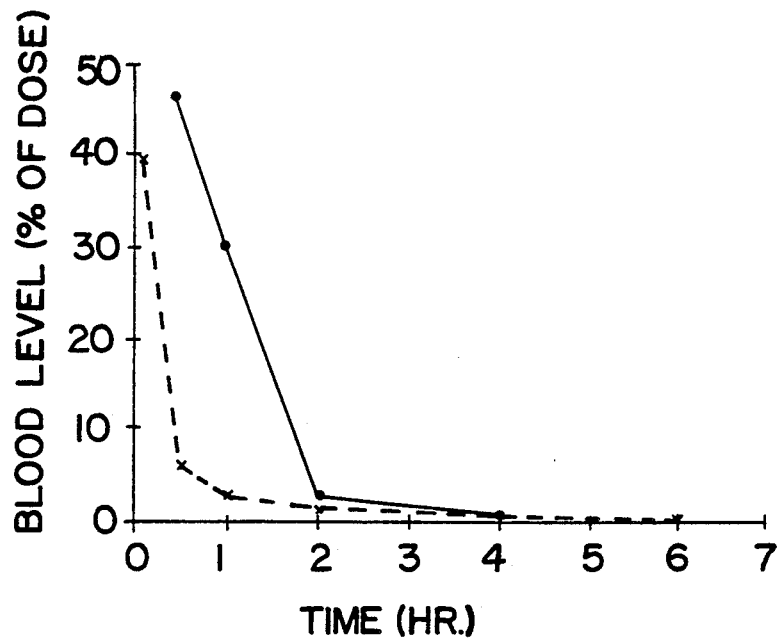
FIGS. 1, 2, 3, 4 and 5 respectively show the relationship between elapsed time and blood drug concentration after intravenous administration to rats of the liposome compositions obtained in Examples 1, 2, 3, 4 and 6.
Figure 2:
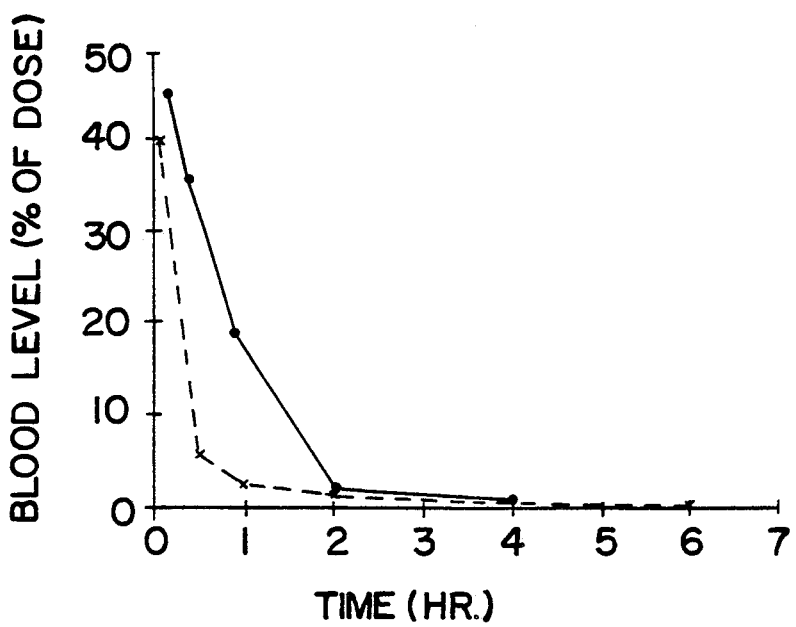
Figure 3:
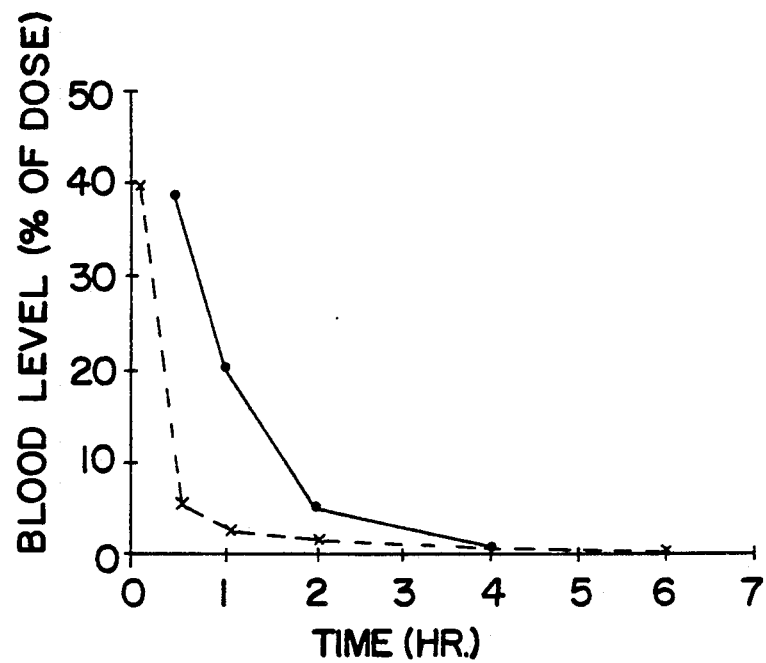
Figure 4:
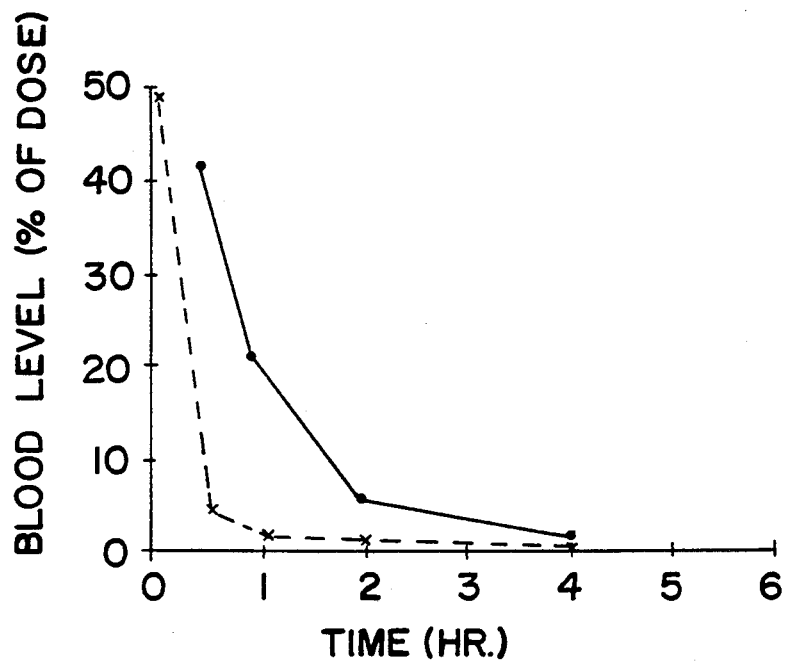
Figure 5:
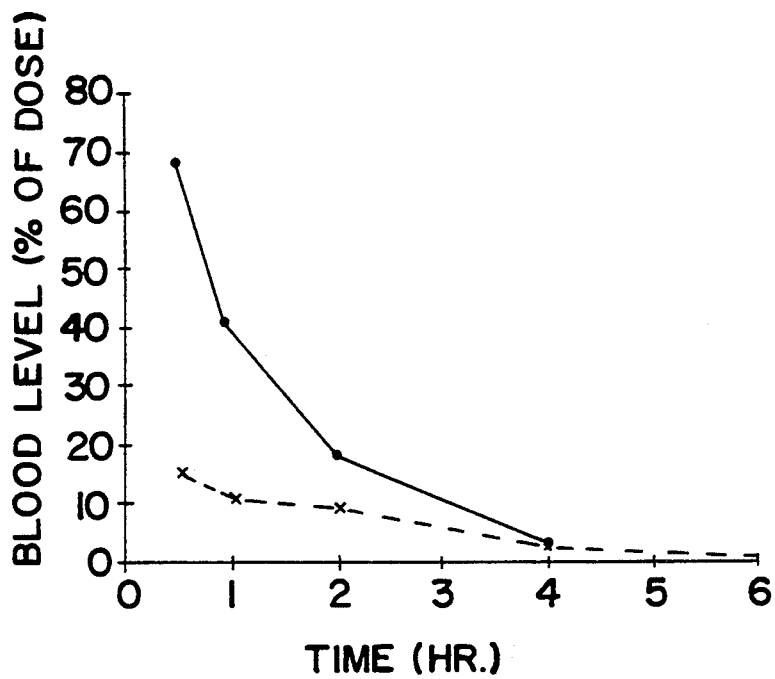

The present invention will now be described in more detail by means of the following working examples, test examples and experimental examples. Note that the ganglysoides used in these examples were all produced by Sigma Co. by extraction and purification from bovine brains [Biochemica et Biophysica Acta, 60, 359–365 (1962)].

Phase transition temperature was determined by differential thermal analysis.

EXAMPLE 1

270 mg of DPPC, 30 mg of DSPC and 30 mg of ganglyoside were dissolved in 70 ml of a 1:1 mixed solution of chloroform and isopropyl ether in a 1 l beaker. To this solution was added 10 ml of a 6-carboxyfluorescein (6-CF) solution, pH 7, prepared so that it had the same osmotic pressure as physiological saline. This mixture was emulsified using a probe-type ultrasonic shaker (Ohtake) to yield a W/O emulsion. Ultrasonication at 50 W for 30 seconds was repeated 10 times. The emulsion thus obtained was placed in a rotary evaporator and the organic solvent was distilled off at 60° C. under reduced pressure to yield REV. The evaporator was adjusted so that the degree of vacuum decreased as the organic solvent evaporated to prevent bumping. The small amount of organic solvent that remained in REV was then distilled off while blowing nitrogen gas. The obtained REV was diluted to 10 ml with an appropriate amount of physiological saline, filtered through a 1.2-micron filter (Acrodisc, Gelman), and dialyzed with a dialysis membrane (Spectrapor, Spectrum Medical) against physiological saline for 24 hours to yield the 6-CF-entrapping liposome composition of the present invention. Quantitative determination of liposome-entrapped 6-CF (Note 1) revealed a 6-CF entrapment ratio of 21.2%. The liposome membrane had a phase transition temperature of 42.3° C.

(Note 1) Quantitative determination of 6-CF in liposome and calculation of entrapment ratio 0.1 ml of liposome was diluted 100-fold with a phosphate-buffered physiological saline (PBS, pH 7.2) and further diluted 100-fold was PBS containing 0.02% Triton X-100, followed by heating for 30 minutes at 60° C. to destroy the liposome. The fluorescence intensity of the solution was measured (Hitachi F3000 fluorospectrometer, excitation wavelength=494 nm, determination wavelength=515 nm) to determine the total 6-CF content in the liposome dispersion. Separately, 0.1 ml liposome was diluted 10,000-fold with PBS; a 2.5-ml portion of this dilution was filtered through a centrifugal filter (Centrisart, SM 13249E, Sartorius); the fluorescence intensity of the resulting filtrate was measured to determine the amount of unincorporated free 6-CF that remained in the liposome dispersion.

Entrapment ratio =

$$\frac{\text{(total 6-CF content in liposome)} - \text{(free 6-CF content in liposome)}}{\text{(amount of 6-CF used to prepare the liposome)}} \times 100$$

EXAMPLE 2

The procedure of Example 1 was followed, but 15 mg of ganglyoside was used in place of 30 mg of ganglyoside, to yield a liposome composition entrapping 6-CF at a 24.4% entrapment ratio and having a 42.5° C. phase transition temperature.

EXAMPLE 3

The procedure of Example 1 was followed, but 45 mg of ganglyoside was used in place of 30 mg of ganglyoside to yield a liposome composition entrapping 6-CF at a 18.3% entrapment ratio and having a 42.1° C. phase transition temperature.

EXAMPLE 4

The procedure of Example 1 was followed, but 210 mg of DPPC and 90 mg of DSPC were used in place of 270 mg of DPPC and 30 mg of DSPC, to yield a liposome composition entrapping 6-CF at a 31.7% entrapment ratio and having a 44.7° C. phase transition temperature.

EXAMPLE 5

The procedure of Example 1 was followed, but ganglyoside was not dissolved in a mixed solution of chloroform and isopropyl ether but dispersed in the 6-CF aqueous solution, to yield a liposome composition entrapping 6-CF at a 22.5% entrapment ration and having a 42.3° C. phase transition temperature.

EXAMPLE 6

360 mg of DPPC, 40 mg of DSPC and 40 mg of granglyoside were dissolved in 40 ml of chloroform in a 1 l beaker. The organic solvent was distilled off using a rotary evaporator to form a liquid film on the glass wall. The trace amount of organic solvent that remained in the film was removed by blowing nitrogen gas. The film thus prepared, together with 10 ml of a 6-CF aqueous solution as used in Example 1 maintained at 60° C., was subjected to vortex treatment to yield MLV. This MLV was ultrasonicated at 50 W power using the probe-type ultrasonic shaker used in Example 1 for about 10 minutes to yield SUV, which was then filtered and dialyzed in the same manner as Example 1 to yield a liposome composition entrapping 6-CF at a 4.9% entrapment ratio and having a 42.3° C. phase transition temperature.

EXAMPLE 7

The procedure of Example 6 was followed, but a 500 μg/ml cisplatin (CDDP) solution in physiological saline was used in place of the 6-CF aqueous solution, to yield a liposome composition entrapping CDDP at a 23.0% entrapment ratio (Note 2) and having a 42.3° C. phase transition temperature.

(Note 2) Method of determining CDDP content in liposome 0.1 ml of liposome was dispersed in 0.5 ml of physiological saline; 2.5 ml of the dispersion was frozen and heated; about 2.5 ml of the obtained disrupted liposome solution was filtered through Centrisalt. To 0.1 ml of the resulting filtrate 2 ml of a 0.1N NaOH solution containing 10% diethyl dithiocarbamate (DDTC) was added, and this mixture was left at room temperature for 30 minutes. The resulting adduct was extracted with 5 ml of n-hexane; the extract was assayed by HPLC (column, Zorbax CN; eluent, n-hexane/isopropyl alcohol=8/2; UV=250 nm) to determine the total CDDP content of the liposome dispersion. Separately, the approx. 2.5 ml portion of liposome dispersion that remained was filtered through Centrisalt, followed by the above procedure to yield an adduct, and the free CDDP not entrapped in the liposome in the dispersion was quantified.

EXAMPLE 8

The procedure of Example 10 followed, but a mixed solution of 25 mM 6-CF and 250 μg/ml CDDP was used in place of the CDDP solution, to yield a liposome composition entrapping 6-CF and CDDP at respective entrapment ratios of 19.2% and 18.6% and having a 42.3° C. phase transition temperature.

EXAMPLE 9

The procedure of Example 7 was followed, but 15 mg of ganglyoside was used in place of 30 mg of ganglyoside, to yield a liposome composition entrapping CDDP at a 20.2% entrapment ratio and having a 42.5° C. phase transition temperature.

EXAMPLE 10

The procedure of Example 8 was followed, but 15 of ganglyoside was used place of 30 mg of ganglyoside, to yield a liposome composition entrapping 6-CF and CDDP at respective entrapment ratios of 17.6% and 18.0% and having a 42.5° C. phase transition temperature.

EXAMPLE 11

The procedure of Example 7 was followed, but 45 mg of ganglyoside was used in place of 30 mg of ganglyoside, to yield a liposome composition entrapping CDDP at a 19.7% entrapment ratio and having a 42.1° C. phase transition temperature.

EXAMPLE 12

The procedure of Example 8 was followed, but 45 mg of ganglyoside was used in place of 30 mg of ganglyoside, to yield a liposome composition entrapping 6-CF and CDDP at respective entrapment ratios of 18.8% and 17.6% and having a 42.1° C. phase transition temperature.

EXAMPLE 13

The procedure of Example 7 was followed, but 210 mg of DPPC and 90 mg of DSPC were used in place of 270 mg of DPPC and 30 mg of DSPC, to yield a liposome composition entrapping CDDP at a 24.1% entrapment ratio and having a 44.7° C. phase transition temperature.

EXAMPLE 14

The procedure of Example 8 was followed, but 210 mg of DPPC and 90 DSPC were used in place of 270 mg of DPPC and 30 mg of DSPC, to yield a liposome composition entrapping 6-CF and CDDP at respective entrapment ratios of 20.7% and 21.2% and having a 44.7° C. phase transition temperature.

EXAMPLE 15

The procedure of Example 7 was followed, but a solution of CDDP in physiological saline was used in place of the 6-CF aqueous solution used in Example 6, to yield a liposome composition entrapping CDDP at a 7.2% entrapment ratio and having a 42.3° C. phase transition temperature.

EXAMPLE 16

The procedure of Example 8 was followed, but a mixed solution of 6-CF and CDDP was used in place of the CDDP solution used in Example 15, to yield a liposome composition entrapping 6-CF and CDDP at respective entrapment ratios of 6.8% and 5.9% and having a 42.5° C. phase transition temperature.

EXAMPLE 17

The procedure of Example 1 was followed, but a 308 μg protein/ml interleukin 2 (IL-2) aqueous solution (solution type: 25 mM ammonium acetate solution, pH 6) was used in place of the 6-CF solution, to yield a liposome composition entrapping IL-2 at a 20.1% entrapment ratio (Note 3). Note that free IL-2 in the liposomes was separated by centrifugation (Sorvall, at 50,000 g, for 30 minutes).

(Note 3) Method of determining IL-2 content in liposomes

To IL-2-entrapping liposomes ultracentrifugated to remove free IL-2, an equal amount of a 0.4% (V/V) Triton X-100 aqueous solution was added, followed by incubation at 37° C. for 30 minutes to disrupt the liposomes. The released IL-2 or ultracentrifugally separated supernatant was assayed by HPLC (column, Ultrapore; UV = 210 nm) on a density gradient. The HPLC eluents used were a solution of 0.1% (V/V) trifluoroacetic acid in acetonitrile/water (40/60 V/V) (Eluent A) and another solution of 0.1% (V/V) trifluoroacetic acid in acetonitrile/water (65/35 V/V) (Eluent B); gradient elution was conducted using the following conditions:

| Time | Eluent A | Eluent B |
| --- | --- | --- |
| 0 min. | 90% | 10% |
| 20 min. | 0% | 100% |
| 25 min. | 0% | 100% |
| 30 min. | 90% | 10% |

Flow rate: 0.9 ml/min.

EXAMPLE 18

The procedure of Example 17 was followed, but a mixed solution of 25 mM 6-CF and 154 μg protein/ml IL-2 was used in place of the IL-2 solution, to yield a liposome composition entrapping 6-CF and IL-2 at respective entrapment ratios of 18.7% and 19.9% and having a 42.3° C. phase transition temperature.

EXAMPLE 19

The procedure of Example 1 was followed, but a 100 μg/ml ansamitocin solution in physiological saline was used in place of the 6-CF solution, to yield a liposome composition entrapping ansamitocin and having a 42.3° C. phase transition temperature.

EXAMPLE 20

The procedure of Example 1 was followed, but a 5 mg/ml methotrexate solution in physiological saline was used in place of the 6-CF solution, to yield a liposome composition entrapping methotrexate and having a 42.3° C. phase transition temperature.

EXAMPLE 21

The procedure of Example 1 was followed, but a 200 μg/ml mitomycin C solution in physiological saline was used in place of the 6-CF solution, to yield a liposome composition entrapping mitomycin C and having a 42.3° C. phase transition temperature.

EXAMPLE 22

The procedure of Example 1 was followed, but a 1 mg/ml adriamycin solution in physiological saline was used in place of the 6-CF solution, to yield a liposome composition entrapping adriamycin and having a 42.3° C. phase transition temperature.

EXAMPLE 23

The procedure of Example 1 was followed, but a 3 mg/ml bleomycin solution in physiological saline was used in place of the 6-CF solution, to yield a liposome composition entrapping bleomycin and having a 42.3° C. phase transition temperature.

EXPERIMENTAL EXAMPLE 1-1

Ganglyoside-free liposomes corresponding to respective liposomes obtained in the above Examples 1, 2, 3, 4 and 6 were prepared. Also, the procedure of Example 1 was followed, but 250 mg of yolk lecithin, 40 mg of cholesterol and 40 mg of ganglyoside were used in place of 270 mg of DPPC, 30 mg of DSPC and 30 mg of ganglyoside, to yield a liposome composition. A ganglyoside-free liposome composition corresponding to this liposome composition was then prepared.

EXPERIMENTAL EXAMPLE 1-2

Figure 6:
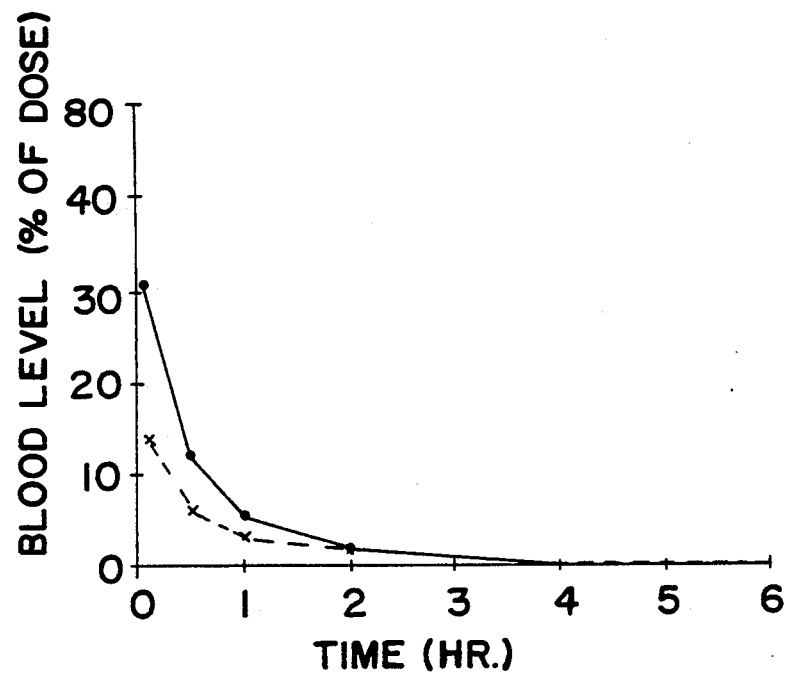
FIG. 6 shows the time course of blood concentration of the liposome composition obtained by the method of Experimental Example 1-1. In these figures, --- —represents ganglyoside-containing liposomes, and --- X --- represents ganglyoside-free liposomes. Values of blood concentration are expressed in percent ratio to dose, and 10% of body weight was taken as the total amount of blood.

The liposome compositions obtained in Examples 1, 2, 3, 4 and 6 and corresponding ganglyoside-free liposome compositions were each intravenously administered to rats in amounts of 0.1 to 0.5 ml, and disappearance of 6-CF from blood was monitored (Note 4). The results are shown in FIGS. 1 though 5. The ganglyoside-containing liposomes obtained in Examples (represented by --- --- in the figure) maintained blood 6-CF concentrations higher than those of ganglyoside-free control liposomes (represented by --- X --- in the figures) 30 minutes, 1 and 3 hours after administration, with mean values of increase rate at 6.8, 8.8, and 2.4 times, respectively. On the other hand, as seen in FIG. 6, when liposome compositions were prepared using egg yolk lecithin and cholesterol., 6CF in the ganglyoside-containing liposomes (represented by --- --- in the figures) and 6CF in the ganglyoside-free liposomes (represented by --- X --- in the figures) were both found to disappear from blood rapidly. As demonstrated by these results, the method of liposome production of the present invention, using a phospholipid with saturated acyl group and a glycolipid with sialic acid group, can be judged efficient and highly practicable for retarding liposome disappearance from blood after its intravenous administration.

EXPERIMENTAL EXAMPLE 1-3

The liposome compositions used in Experimental Example 1-2 were each intravenously administered to rats. One hour later, liver 6-CF concentration was measured to determine liposome dispersion in RES (Note 4). The results obtained are shown in Table 1. These results demonstrate that liposome disappearance from blood was retarded and liposome distribution in the liver and other RES organs was reduced.

TABLE 1

| | 6-CF Concentration (%) in the Liver, Determined One Hour after Adminstration | |
|---|---|---|
| Liposome type | With gagnglyoside | Without ganglyoside |
| Example 1 | 20.8 | 30.1 |
| Example 2 | 21.6 | 30.1 |
| Example 3 | 18.2 | 30.1 |
| Example 4 | 22.3 | 59.7 |
| Example 6 | 15.9 | 44.7 |
| Yolk lecithin-cholesterol | 29.0 | 33.9 |

(Note 4) Methods of determining blood and liver 6-CF liposome concentrations

A blood dispersion was prepared by adding 10 ml PBS to 0.2 ml of heparin-treated tail vein blood. This dispersion was centrifuged (3,000 rpm, 10 min). To 5 ml of the resulting supernatant, 0.05 ml of 2% Triton X-100 was added, followed by heating at 60° to 70° C. to destroy the liposome. The fluorescence intensity of the released 6-CF was measured to determine the blood liposome concentration. Also, a liver excised after laparotomy and exsanguination was immersed in PBS containing 0.02% Triton X-100 to yield 100 ml, then disrupted using a tissue homogenizer (Polytron, Kinematica), after which it was heated to 60° to 70° C. so that 6-CF release from the liposome in the homogenate. This homogenate was ultracentrifuged (50,000 g, 10 min), diluted 20- to 50-fold, and filtered through a 0.45-micron membrane filter (Acrodisk, Gelman). The fluorescence intensity was then measured to determine liver liposome concentration.

EXPERIMENTAL EXAMPLE 4-4

The liposome compositions obtained in Examples 1, 2, 3 and 4 and corresponding ganglyoside-free liposome compositions thereto were each diluted 10,000-fold with PBS. The amount of 6-CF released from liposomes while heating each dilution was continuously measured using a fluorometer connected to the heating system in order to monitor the phase change (from gel to liquid crystal) in the liposome membranes. The thermal release initiation temperatures determined on release curves are shown in Table 2.

TABLE 2

| Liposome Membrane Phase Transition Temperature (°C.) and Temperature (°C.) of Initiation of 6-CF Thermal Release from Liposomes | | |
|---|---|---|
| Liposome Type | Phase Transition Temp. | Thermal Release Initiation Temp. |
| Example 1 (with ganglyoside) | 42.3 | 38.0 |
| Example 2 (with ganglyoside) | 42.5 | 37.8 |
| Example 3 (with ganglyoside) | 42.1 | 36.2 |
| Example 1, 2, 3, but without ganglyoside | 42.8 | 38.2 |
| Example 4 (with ganglyoside) | 44.7 | 38.0 |
| Example 4, but without ganglyoside | 45.5 | 38.4 |

EXPERIMENTAL EXAMPLE 2-1

Ganglyoside-free liposome compositions were prepared respectively corresponding to the liposome compositions of Examples 8, 10, 14 and 16.

EXPERIMENTAL EXAMPLE 2-2

The liposome compositions obtained in Examples 8, 10, 14 and 16 and ganglyoside-free liposome compositions respectively corresponding thereto were each intravenously administered to rats in amounts of 0.1 to 0.5 ml, and liposome disappearance from blood was monitored by measuring blood 6-CF concentration during the 6-hour period following the administration. The ganglyoside-containing liposomes maintained blood concentrations higher than those of ganglyoside-free control liposome compositions 30 minutes, and 1 and 2 hours after administration, with mean values of increase rate at 2.2, 9.8, and 3.7 times, respectively. Also, blood CDDP concentration was measured during the 1-hour period following the administration (Note 5); it was as high as 6-CF concentration, suggesting that CDDP, together with 6-CF, was incorporated in the liposomes in blood. As demonstrated by these results, the method of liposome production of the present invention, which uses a phospholipid with saturated acyl group and a glycolipid with sialic acid group for the liposome membrane composition, can be judged efficient and highly practicable for retarding liposome disappearance from blood after its intravenous administration.

(Note 5) Method of determining blood CDDP concentration

A blood dispersion was obtained by adding 2 ml PBS to 0.2 ml of heparin-treated tail vein blood, followed by centrifugation. To 1 ml of the separated supernatant 1 ml of a DDTC solution was added, and the total CDDP content in blood was determined using the above procedure for CDDP determination.

What we claim is:

1. A liposome composition entrapping a drug in liposome which has a membrane constituted by a phospholipid of which the acyl groups thereof are saturated acyl groups and ganglyosides, said membrane having a phase transition temperature in the range of about 40° to 55° C.

2. The composition according to claim 1, wherein the phospholipids are glycerophospholipids or sphingeophospholipids.

3. The composition according to claim 1, wherein the phospholipid has two acyl groups which are saturated alkyls having 8 or more carbon atoms, acyl groups at least one of which is a saturated alkyl group having 10 or more.

4. The composition according to claim 1, wherein said composition is contained within a drug delivery system.

5. The composition according to claim 1, wherein the drugs are antitumor agents, lymphokines, physiologically active peptides, antibiotics, vitamins, antiprotozoan drugs, enzymes, anticoagulation agents antiallergic agents, or immunopotentiating agents.

6. The composition according to claim 1, wherein the antitumor agents are platinum compounds.

7. The composition according to claim 6, wherein the platinum compound is cisplatin.

8. The composition according to claim 1 wherein the amount of the ganglyoside in said liposome composition is in the range of about 0.5 to 50 weight parts per 100 weight parts of the phospholipid.

* * * * *